(12) United States Patent
Beverly

(10) Patent No.: US 6,945,650 B2
(45) Date of Patent: Sep. 20, 2005

(54) ALIGNMENT SYSTEM FOR HAND-HELD OPHTHALMIC DEVICE

(75) Inventor: David Beverly, Alden, NY (US)

(73) Assignee: Reichert, Inc., Depew, NY (US)

( * ) Notice: Subject to any disclaimer, the term of this patent is extended or adjusted under 35 U.S.C. 154(b) by 439 days.

(21) Appl. No.: 10/117,507

(22) Filed: Apr. 5, 2002

(65) Prior Publication Data

US 2003/0086060 A1 May 8, 2003

Related U.S. Application Data

(63) Continuation-in-part of application No. 09/992,756, filed on Nov. 6, 2001, now Pat. No. 6,669,340.

(51) Int. Cl.[7] .................................................. A61B 3/14
(52) U.S. Cl. ......................................................... 351/208
(58) Field of Search .............................. 351/205, 206, 351/208–214, 221; 600/399–401, 504

(56) References Cited

U.S. PATENT DOCUMENTS

| | | | |
|---|---|---|---|
| 3,585,849 A | | 6/1971 | Grolman |
| 3,756,073 A | | 9/1973 | Lavallee et al. |
| 4,597,649 A | | 7/1986 | Swaniger et al. |
| 4,665,923 A | | 5/1987 | Kobayashi |
| 4,881,807 A | | 11/1989 | Luce et al. |
| 4,995,393 A | * | 2/1991 | Katsuragi et al. ............ 600/401 |
| 5,625,428 A | | 4/1997 | Isogai |
| 5,976,096 A | * | 11/1999 | Shimizu et al. .............. 600/504 |
| 6,022,108 A | * | 2/2000 | Yoshida et al. .............. 351/208 |
| 6,042,544 A | | 3/2000 | Miwa et al. |
| 6,220,706 B1 | | 4/2001 | Foley |
| 6,361,495 B1 | | 3/2002 | Grolman |

* cited by examiner

Primary Examiner—George Manuel
(74) Attorney, Agent, or Firm—Hodgson Russ LLP

(57) ABSTRACT

An alignment system for an ophthalmic instrument comprises an optical axis along which an operator can directly view the patient's eye and the patient can fixate on a dark fixation target surrounded by a bright background that helps to illuminate the eye for operator viewing. A position detection system utilizing stored geometrical relationships determined by multiple regression during instrument calibration computes X-Y-Z alignment status of the instrument relative to a patient's eye based on local x-y position information from a pair of lateral detectors receiving corneally reflected light from a corresponding pair of lateral light sources. A heads-up display image is provided along an optical axis of the instrument for supplying instructive cues to an operator for moving the instrument to achieve alignment based on signal information from the position detection system, whereby the operator sees both a direct macro-image of the patient's eye and the display image. The alignment system is particularly suitable for use in hand-held ophthalmic instruments.

27 Claims, 11 Drawing Sheets

ALIGNMENT SYSTEM FOR HAND-HELD OPHTHALMIC DEVICE

CROSS-REFERENCE TO RELATED APPLICATIONS

This is a continuation-in-part application claiming benefit under 35 U.S.C. §120 of U.S. patent application Ser. No. 09/992,756 filed Nov. 6, 2001, which is currently U.S. Pat No. 6,669,340.

FIELD OF THE INVENTION

The present invention relates generally to alignment systems for enabling an operator to position an ophthalmic instrument relative to an eye of a patient, and more particularly to an alignment system that is well-suited for use in a hand-held ophthalmic instrument and that provides an operator with a direct view of a patient's eye as a positioning aid.

BACKGROUND OF THE INVENTION

Alignment systems for use by an operator in locating an ophthalmic instrument relative to an eye of a patient vary in complexity. In instruments where alignment is critical to measurement accuracy, for example in non-contact tonometers, it is commonplace to provide means for projecting a visible fixation target image along a measurement axis of the instrument to direct the patient's gaze, and to further provide an opto-electronic position detection system capable of sensing the position of the instrument relative to the eye. Where the ophthalmic instrument is a non-contact tonometer having a discharge tube for directing a fluid pulse at the eye, X-Y alignment is typically achieved by aligning an axis of the discharge tube to intersect with the corneal vertex, and Z alignment is achieved by positioning a fluid exit end of the discharge tube at a predetermined distance from the corneal vertex.

U.S. Pat. No. 3,756,073 to Lavallee et al. describes a non-contact tonometer having a target projecting system that projects an image of a target along an alignment axis through an objective lens to the image plane of the objective lens. Consequently, when the image plane of the objective lens is coincident with the center of curvature of the patient's cornea, a corneal virtual or mirror image of the target is reimaged by the objective lens and a telescope lens in the plane of a circle reticle on the alignment axis. An operator looking through an eyepiece along the alignment axis toward the eye can see the retro-reflected target image superimposed on the circle reticle, and aligns the instrument laterally and vertically (X-Y alignment) by centering the target image with respect to the reticle markings. According to this system, the corneal surface under observation is limited to a desired small portion of the entire corneal surface. The '073 patent also describes a passive "go/no go" alignment confirmation system comprising an infra-red LED cooperating with an alignment detector located behind a pinhole aperture, whereby the detector generates a trigger signal upon alignment.

A more sophisticated opto-electronic alignment system for use in locating an ophthalmic instrument relative to an eye is taught in U.S. Pat. No. 4,881,807 to Luce et al. According to this system, and other systems of the prior art, triangulation is used to gauge the three-dimensional location of the eye relative to the instrument. By way of example, the aforementioned U.S. Pat. No. 4,881,807 discloses a system wherein two light sources arranged on opposite sides of the eye illuminate the eye with divergent rays, and a pair of CCD area detectors each comprising a two-dimensional array of light-sensitive pixels are arranged behind associated pinhole apertures to receive a small bundle of reflected rays originating from a corresponding one of the light sources. A local x-y location where the light strikes the CCD array is determined by identifying the pixel registering the peak response signal. The local x-y locations where light strikes each CCD array and specifications describing the predetermined geometric arrangement of the system components are provided as inputs to a microprocessor, which then calculates the amount of movement in the global X, Y, and Z directions necessary to achieve alignment. A video image detector is also provided to supply a macro-image of the eye to a CRT display, and output from the alignment CCD electronics is coupled into the CRT display electronics to provide alignment illumination spot symbols on the video display image.

Known alignment systems that actively monitor X, Y, and Z alignment status do not afford the operator a direct macro view of the eye along an alignment axis or main optical axis of the instrument for alignment purposes. In fact, many prior art systems rely on generating and displaying a video image of the eye and superimposing alignment cues in the displayed video image for moving the instrument to achieve alignment. This approach requires instrumentation that adds to the size, weight, and expense of the instrument, thereby rendering such systems impractical for use in hand-held ophthalmic devices.

So called "heads up displays" or HUDs are known in the field of aviation for projecting symbols and cues regarding flight parameters into the pilot's field of view while the pilot is looking forward through the windscreen, as opposed to downward at the instrument panel. These display systems require multiple optical systems to modify magnification and focus position for a user viewing a distant object through a close display, and are not suited for use in connection with alignment of an ophthalmic instrument.

SUMMARY OF THE INVENTION

Therefore, it is an object of the present invention to provide an alignment system for an ophthalmic instrument that affords the operator a direct view of the patient's eye along an optical axis of the instrument.

It is another object of the present invention to provide an alignment system for an ophthalmic instrument that includes an instructive display image superimposed with the directly viewed real image of the eye in the operator's field of view to supply real time alignment cues as feedback to the operator during alignment.

It is another object of the present invention to provide an alignment system for an ophthalmic instrument that affords the operator a direct view of the patient's eye along an optical axis of the instrument and an instructive display image superimposed in the operator's field of view while simultaneously presenting a fixation target to the patient along the optical axis.

It is a further object of the present invention to provide an alignment system for an ophthalmic instrument that is lightweight and has few components for incorporation into a hand-held ophthalmic device.

It is yet a further object of the present invention to provide an alignment system for an ophthalmic instrument that is relatively inexpensive to manufacture.

An alignment system according to a preferred embodiment further comprises an a focal position detection system for determining X-Y-Z alignment status of the instrument relative to the patient's eye. The position detection system comprises first and second light sources on opposite sides of the central optical axis of the instrument, and corresponding first and second light-sensitive area detectors positioned to receive light from an associated light source after it has been reflected by the cornea. The detectors provide signal information indicative of the local x-y position of an illumination spot formed thereon. In a preferred embodiment, the first and second detectors are quad-cell detectors having four quadrants, and the illumination spot size is about the size of one quadrant, whereby the x-y position can be determined based on the four signal levels generated by the quadrants. Collector lenses after each light source and in front of each detector minimize vergence in the light beam as it illuminates the eye and as it arrives at a detector.

The local x-y data from each detector are then provided as input to a series of stored geometrical relationships determined during instrument calibration for giving the X-Y-Z global alignment status of the instrument relative to the eye. The geometrical relationships are multiple regression equations for X, Y, and Z, wherein regression coefficients for each equation are determined by reading local x-y data from the detectors for an artificial eye placed at a plurality of known X-Y-Z positions during calibration. The regression coefficients are stored during calibration and used during normal instrument operation to quickly calculate X, Y and Z coordinates based on local x-y data from the detectors as an operator positions the instrument relative to a patient's eye.

A "heads-up" display is connected to receive the X-Y-Z position data and provide instructional cues to the operator for moving the instrument to achieve alignment. In a current embodiment, the heads-up display comprises a polar array of light emitting diodes selectively illuminated to indicate a desired X-Y movement direction, and a linear array of light emitting diodes selectively illuminated to indicate a desired Z movement direction. An image of the heads-up display is presented to the operator along the instrument optical axis through the use of a beamsplitter that allows a macro-image of the patient's eye to be transmitted as well along the optical axis, whereby the X-Y polar array is arranged circumferentially about the directly viewed macro-image of the eye.

BRIEF DESCRIPTION OF THE DRAWING

The nature and mode of operation of the present invention will now be more fully described in the following detailed description of the invention taken with the accompanying drawing figures, in which.

DETAILED DESCRIPTION OF THE INVENTION

Figure 1:
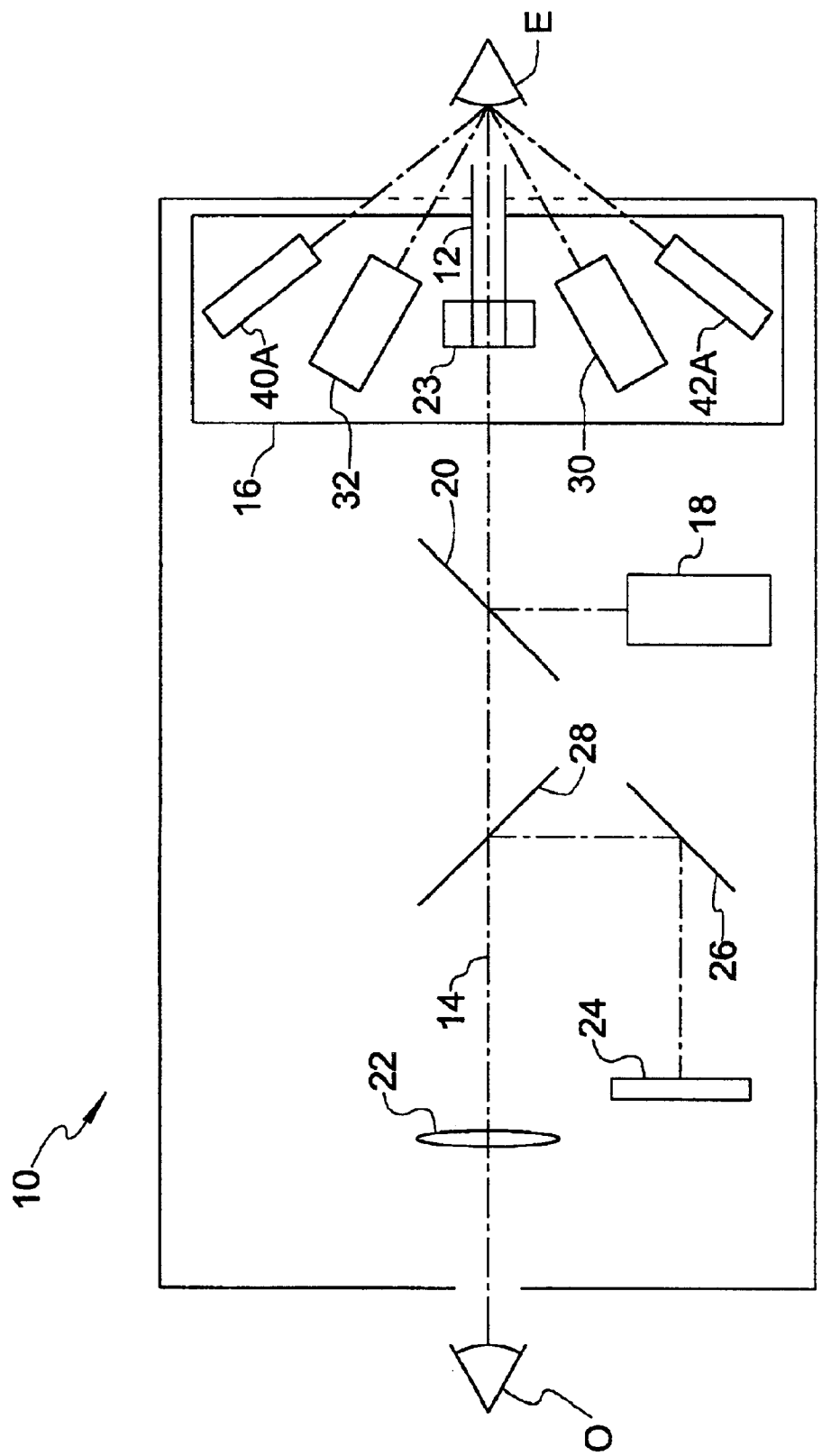
FIG. 1 is an optical schematic diagram of an ophthalmic instrument incorporating an alignment system of the present invention.

In FIG. 1, an ophthalmic instrument incorporating an alignment system of the present invention is illustrated schematically and identified by the reference numeral 10. Instrument 10 is depicted as being a non-contact tonometer operable to discharge a fluid pulse through a fluid discharge tube 12 to cause observable deformation of a patient's cornea for purposes of measuring intraocular pressure. However, the present invention may be implemented in other types of ophthalmic instruments where it is necessary to ascertain the X-Y or X-Y-Z alignment status of the instrument relative to an eye.

Instrument 10 includes an optical axis 14 along which discharge tube 12 is aligned, a nosepiece 16 fixed near a front portion of the instrument for mounting various optical and opto-electronic elements of the instrument as described below, a fixation target projecting system 18 cooperating with a beamsplitter 20 to present a visible fixation target to the patient along optical axis 14, an eyepiece 22 and a macro-lens 23 for enabling an operator 0 to view the patient's eye E through the instrument along optical axis 14, a heads-up display 24, and a mirror 26 cooperating with a beamsplitter 28 to present an image of the heads-up display to the operator along optical axis 14. Macro-lens 23 is preferably a planar-planar lens such that the operator sees the eye in an unmagnified state, however it is possible to use a macro-lens having optical power to provide some other desired field of view with respect to the eye.

Figure 2:
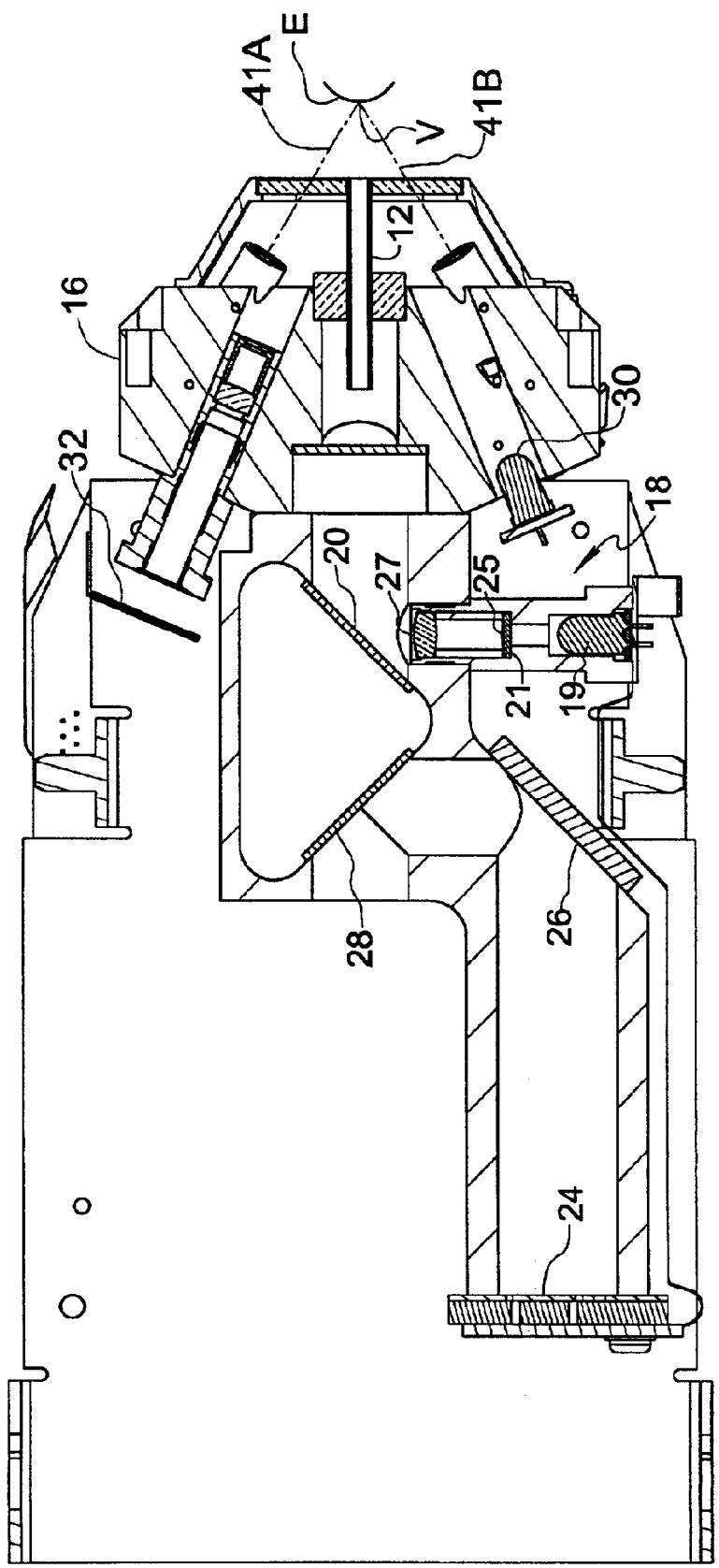
FIG. 2 is a sectional view of an optical block portion of the ophthalmic instrument shown in FIG. 1.

FIG. 2 shows fixation target projecting system 18 in greater detail. An LED 19 emits light that passes through a finely ground diffuser element 21 having a central target dot 25 painted translucent red. The light from diffuser element 21 then passes through a collimating lens 27 before the collimated target light is reflected by beamsplitter 20 to follow optical axis 14. The use of a relatively dark target dot against a bright background field is preferred because the bright background light helps to illuminate the patient's eye E to aid the operator's direct view of the eye along optical axis 14. Additional light sources (not shown) mounted in or near nosepiece 16 may be employed to help illuminate eye E.

Attention is directed now to the elements mounted in or on nosepiece 16. As mentioned above, instrument 10 is illustrated as being a non-contact tonometer, and thus it includes an applanation emitter 30 for obliquely illuminating the eye during discharge of the fluid pulse, and an applanation detector 32 arranged on an opposite side of the eye for receiving light reflected from the cornea and registering a peak signal at the moment the corneal surface is flattened ("applanated") by the fluid pulse. Those familiar with the non-contact tonometers will recognize that applanation emitter 30 and applanation detector 32 are parts of a well-known prior art arrangement for determining the moment applanation occurs based on reflected light from the corneal surface.

Also within nosepiece 16 are elements of a position detection system forming part of an alignment system according to an embodiment of the present invention. More specifically, the schematic representation of FIG. 1 shows light source 40A on one side of optical axis 14 and a detector 42A on an opposite side of optical axis 14 used for position detection. In actual practice, nosepiece 16 supports a second light source 40B and a second detector 42B, which can be seen in the view of FIG. 3. In the embodiment described at present, light sources 40A and 40B are located just below the horizontal plane containing optical axis 14, while detectors 42A and 423 are located just above the horizontal plane containing optical axis 14, thereby leaving space in the horizontal plane for applanation emitter 30 and applanation detector 32. First light source 40A directs a first beam of light along a first illumination axis 41A for illuminating eye E, and first detector 42A defines a first light-detecting area for receiving an image of first light source 40A formed by light reflected from the eye. Light traveling along first illumination axis 41A passes through a collector lens 44A and is obliquely incident to the generally spherical surface of the cornea, where it is reflected toward first detector 42A. A collector lens 46A in front of first detector 42A substantially collimates the divergent beam coming from the generally spherical surface of the cornea, whereby a spot of illumination is received on the light-detecting area defined by first detector 42A. Essentially, first detector 42A detects an apparent or virtual source behind the cornea. Second light source 40B, second illumination axis 41B, collector lenses 44B and 46B, and second detector 42B form a similar system, and are preferably arranged in opposing symmetry about the vertical plane containing optical axis 14. In a preferred construction, position light sources 40A and 40B and applanation emitter 30 are infrared light-emitting diodes for invisibility to the patient, and are mounted or formed on a single flexible circuit board to allow assembly of the instrument with greater ease. Similarly, first and second detectors 42A, 42B are preferably carried by a flexible circuit board for easy assembly.

Figure 3:
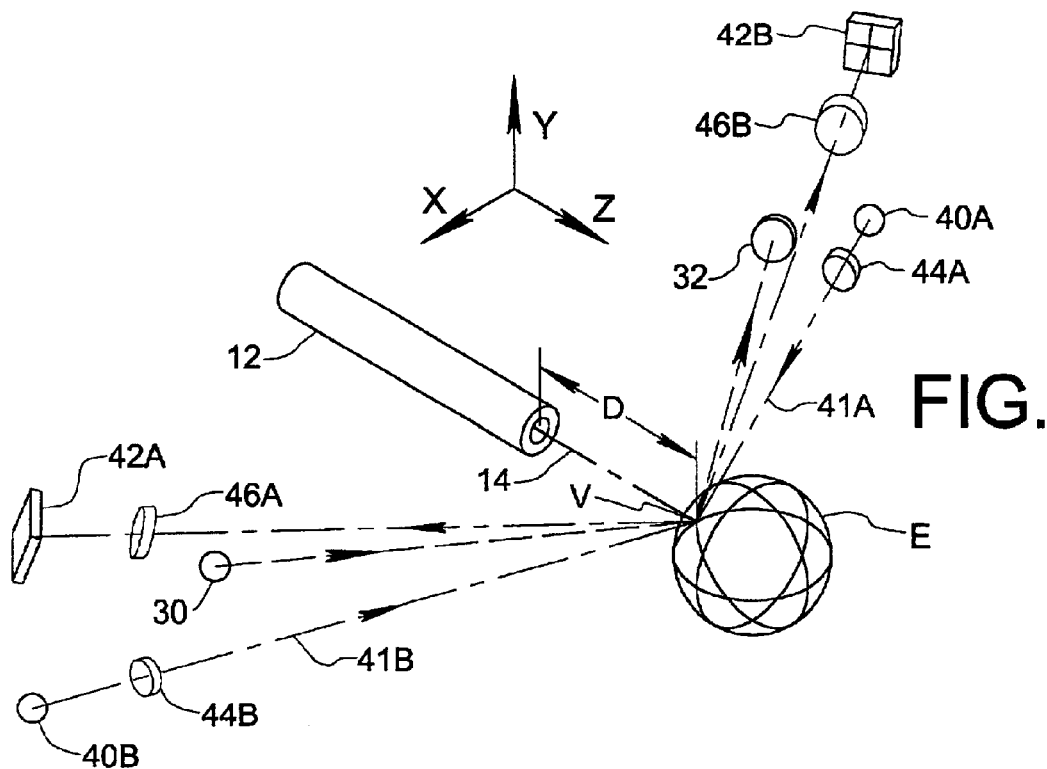
FIG. 3 is a schematic perspective view showing the arrangement of elements of a position detection system forming part of the alignment system in accordance with a preferred embodiment of the present invention.

In the illustration of FIG. 3, the instrument as represented by the exit end of fluid discharge tube 12 and the eye as represented by the corneal vertex V are shown in a state of three-dimensional (X-Y-Z) alignment. In the present embodiment, alignment is achieved when optical axis 14 intersects and is normal to corneal vertex V, and the exit end of fluid discharge tube 12 is a predetermined working distance (firing distance D) away from corneal vertex V in a Z-axis direction. The orientation of first detector 42A and that of second detector 42B are chosen such that the central ray of the corresponding corneally reflected illumination beam is normal to the light-detecting area of the associated detector and arrives substantially at a central point of the light-detecting area when X-Y-Z alignment exists.

Figure 4:
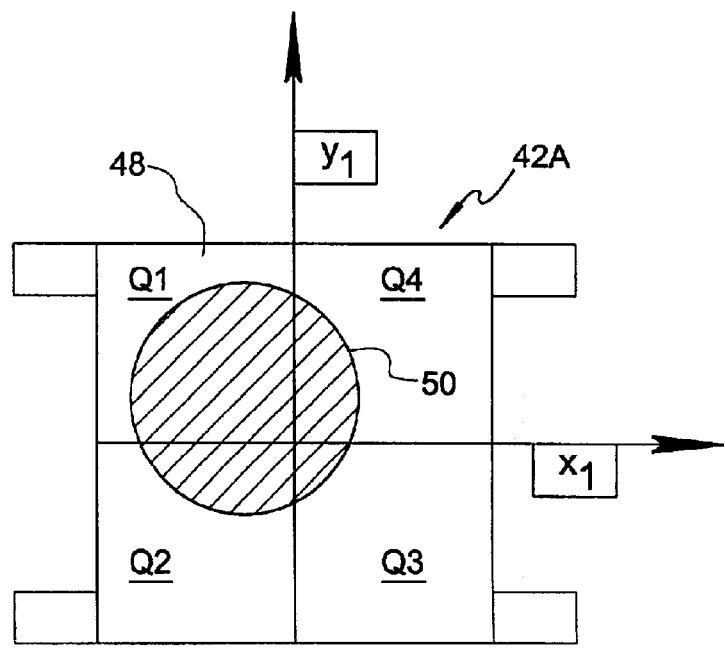
FIG. 4 is a detail view of a quad-cell detector of the position detection system shown in FIG. 3.

FIG. 4 shows a light-detecting area 48 of first detector 42A, with the understanding that the accompanying description also applies as well to second detector 42B. An image of light source 40A appears as a spot 50 on light detecting area 48. In the present embodiment, first detector 42A is a quad-cell detector comprising four quadrants Q1, Q2, Q3, and Q4 each providing a signal proportional to the illumination optical power received thereby. The size of each quadrant is preferably on the order of about 1.3 mm×1.3 mm, with a separation distance of about 0.1 mm between adjacent quadrant edges. The size of illumination spot 50 should be on the order of the size of one quadrant for meaningful x-y resolution. The size of illumination spot 50 will change during Z-axis adjustment as instrument 10 is moved closer to or further away from the eye. Moreover, the rate of change in spot size increases as the instrument moves closer to the eye. Therefore, it is desirable to optimize the system for a range of Z-axis positions centered about the predetermined firing distance D (i.e. +/−2.00 mm) such that the change in spot size for Z-axis positions throughout the range is minimized. Optimization can be carried out by selecting an appropriate front focal length for collector lenses 46A, 46B that causes the light striking detectors 42A, 42B to transition from being slightly convergent to being slightly divergent as the instrument is moved through the range of Z-axis positions toward the eye, wherein the light striking detectors 42A, 42B is approximately collimated when the instrument is at the predetermined firing distance D. In practice, it has been found that the firing distance D should be just beyond the front focal length of collector lenses 46A, 46B.

As will be understood, the signals from quadrants Q1–Q4 of first detector 42A are indicative of the local two-dimensional location $(x_1, y_1)$ of the centroid of spot image 50 in light detecting area 48, and the signals from quadrants Q1–Q4 of second detector 42B are indicative of the local two-dimensional location $(x_2, y_2)$ of a similar spot formed on the light detecting area of the second detector. The local x position is given by comparing the signal strengths from each quadrant as follows:

$$x=(Q3+Q4-Q1-Q2)/(Q1+Q2+Q3+Q4)$$

Likewise, the local y position is given by comparing the signal strengths from each quadrant as follows:

$$y=(Q1+Q4-Q2-Q3)/(Q1+Q2+Q3+Q4).$$

Figure 5:
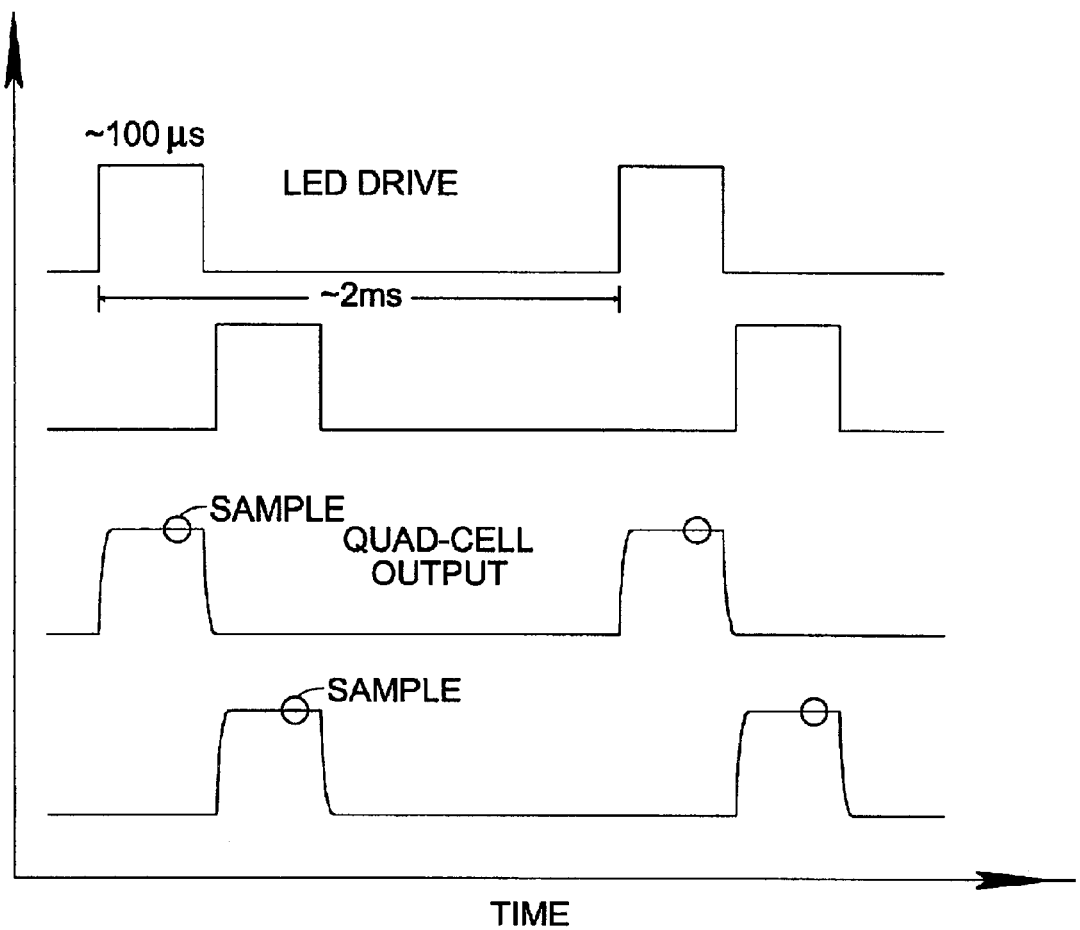
FIG. 5 is an electronic timing diagram relating to illumination and sampling of the quad-cell detector shown in FIG. 4.

In order to avoid interference, provide sufficient illumination intensity, and reduce power consumption, first light source 40A and second light source 40B are illuminated sequentially, and first detector 42A and second detector 42B are sampled sequentially. FIG. 5 is a timing diagram that illustrates that one light source is pulsed for a duration of about 100 µs and then sampled, and then the other light source is pulsed for the same duration and sampled. The cycle is repeated at approximately every 2 ms.

Figure 6:
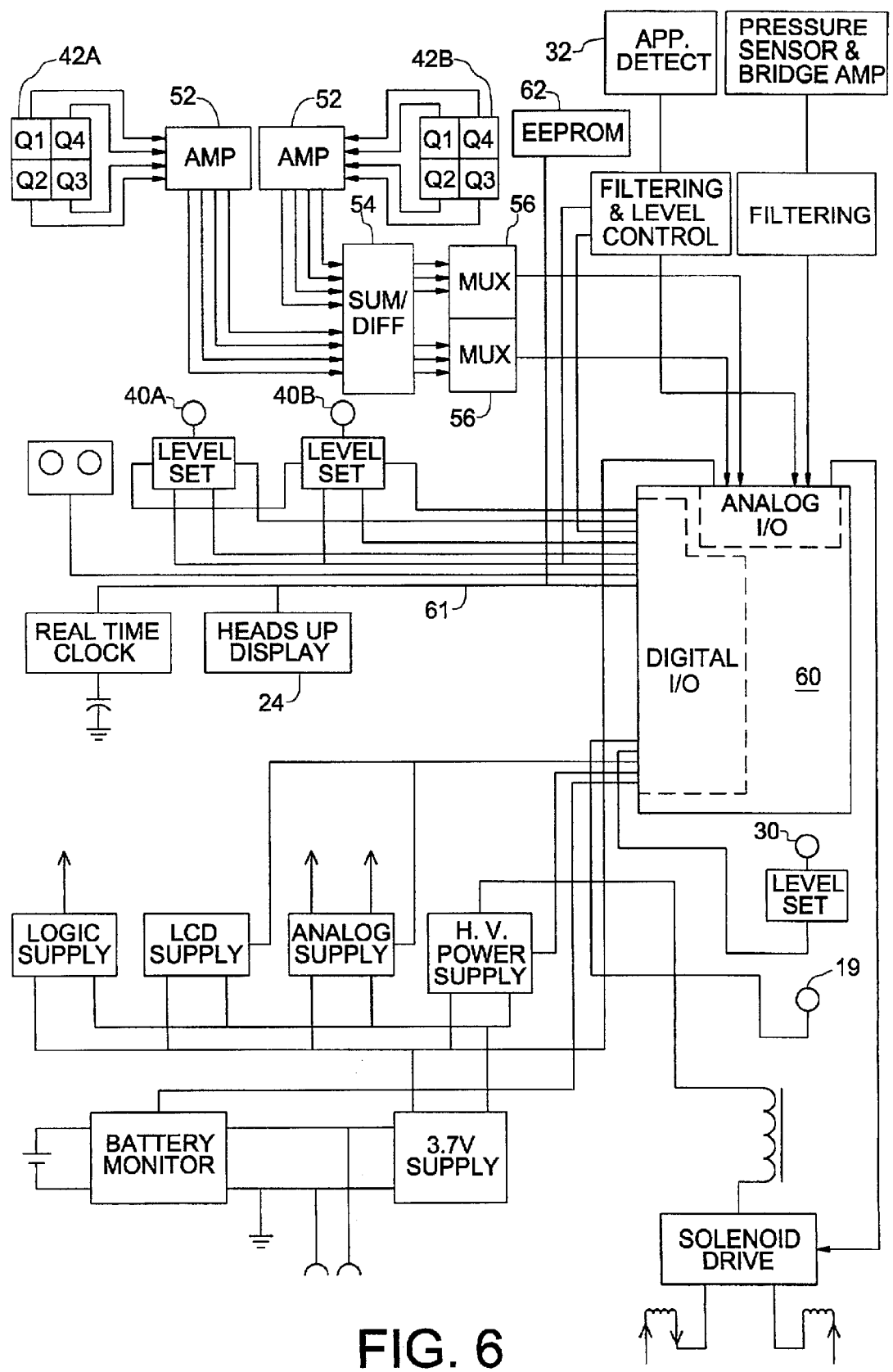
FIG. 6 is an electronic block diagram of the ophthalmic instrument shown in FIG. 1.

Referring also now to FIG. 6, the analog signals from quadrants Q1–Q4 of detectors 42A, 42B are fed to amplifiers 52 and then input to a sum/difference circuit 54. Sum/difference circuit 54 provides three outputs for each position detector 42A, 42B. Two of the outputs are the respective x and y numerators in the above equations, and the third output is the denominator common to both equations. The output signals are multiplexed by a multiplexor 56 and then provided as analog input to a microprocessor 60, which provides on-board analog-to-digital conversion of the signals. Microprocessor 60 is programmed to calculate the final spot locations $(x_1, y_1)$ and $(x_2, y_2)$.

While the present embodiment is described as employing quad-cell detectors, it is possible to substitute other detector types and configurations for purposes of the present invention. For example, a variety of position sensitive devices (PSDs) are commercially available that can provide local x-y signal information. Also, it is possible to arrange four discrete photosensitive detectors in a quadrant configuration to mimic the quad-cell detector described above.

The global X-Y-Z alignment status of ophthalmic instrument 10 relative to the eye is then computed by inputting coordinates $x_1$, $y_1$ from first detector 42A and coordinates $x_2$, $y_2$ from second detector 42B to a plurality of predetermined geometric relationships stored in memory 62 during calibration of instrument 10. More specifically, geometrical relationships giving the global position coordinates X, Y, and Z can be determined by multiple regression as follows:

$$X = R_1 x_1 + R_2 y_1 + R_3 x_2 + R_4 y_2 + R_5,$$

$$Y = R_6 x_1 + R_7 y_1 + R_8 x_2 + R_9 y_2 + R_{10}, \text{ and}$$

$$Z = R_{11} x_1 + R_{12} y_1 + R_{13} x_2 + R_{14} y_2 + R_{15},$$

wherein the regression coefficients $R_1$–$R_{15}$ are found during instrument calibration measurements using an artificial eye.

Figure 7:
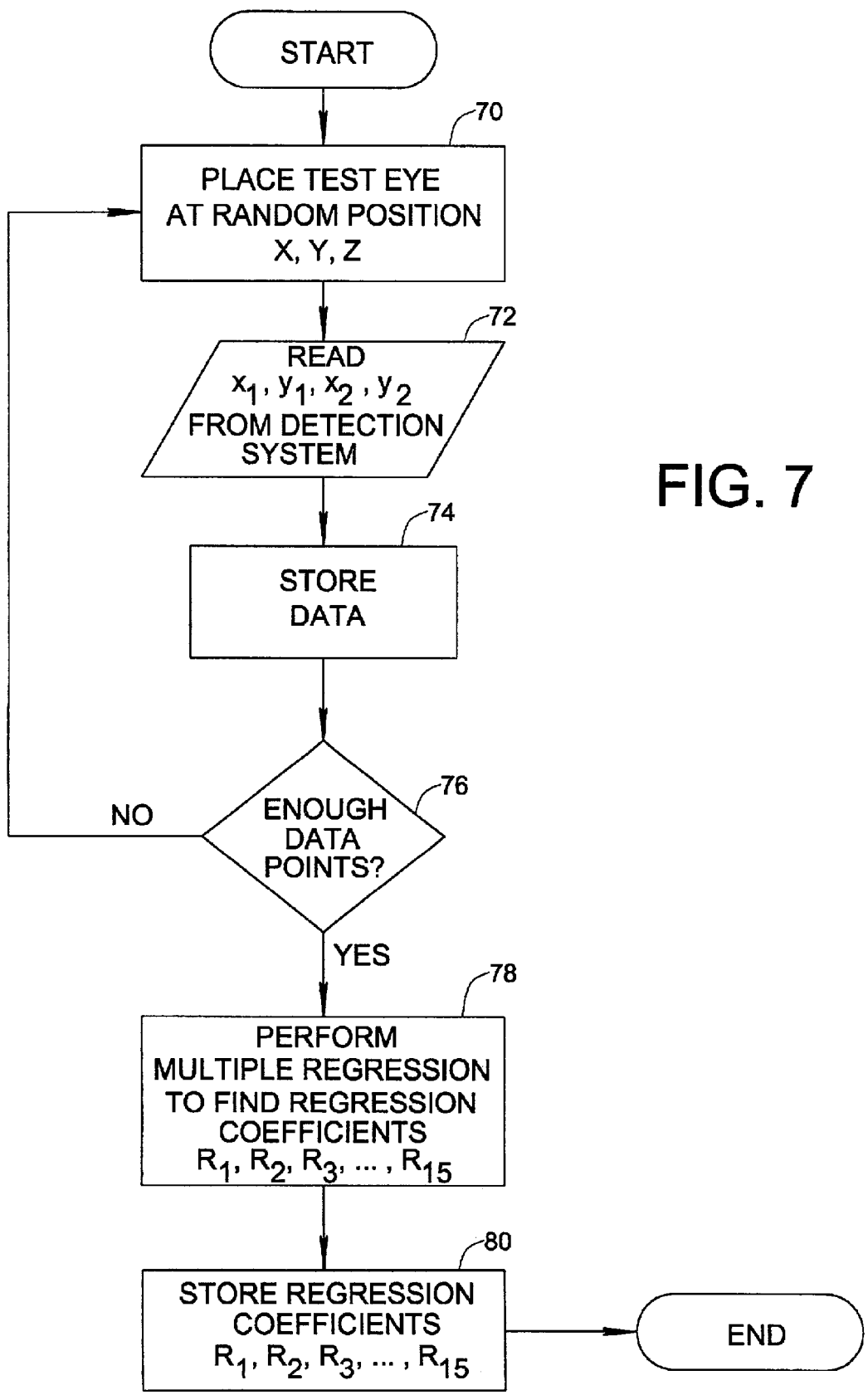
FIG. 7 is a flow diagram of steps followed to calibrate the position detection system shown in FIG. 3.

FIG. 7 is a flow diagram showing the steps followed to calibrate the position detection system of the present invention. First, according to step 70, an artificial "test" eye is placed at a random, known position X, Y, Z relative to instrument 10. Then, as indicated by steps 72 and 74, the local spot positions $(x_1, y_1)$ and $(x_2, Y_2)$ are read from the position detection system and stored in a table with the corresponding known global coordinates X, Y, Z. If a sufficient number of data points have been measured according to query 76, multiple regression is performed in step 78 to find the regression coefficients $R_{1-R15}$, which are then stored in memory pursuant to step 80. If more data points are needed according to query 76, the process returns to step 70 and is repeated. It is preferable to calibrate the position detection system using a large number random locations of the artificial eye, as this will provide greater accuracy in the determination of the regression coefficients, and ultimately provide improved accuracy in the computed X, Y, Z location of a patient's eye.

Primarily because the position detection system of the present invention obviates the need for scanning a CCD array having a large number of pixels, it provides X-Y-Z alignment status information at a much higher repetition rate than systems of the prior art. As noted above, a faster system is particularly useful for alignment of hand-held instruments, which may be actuated to take a measurement as soon as X-Y-Z alignment is confirmed. Thus, the system reduces the lag time between confirmation of alignment and measurement during which further relative movement between the instrument and eye can occur. Moreover, the position detection system of the present invention can be calibrated periodically by manufacturer personnel to ensure alignment accuracy.

Figure 8:
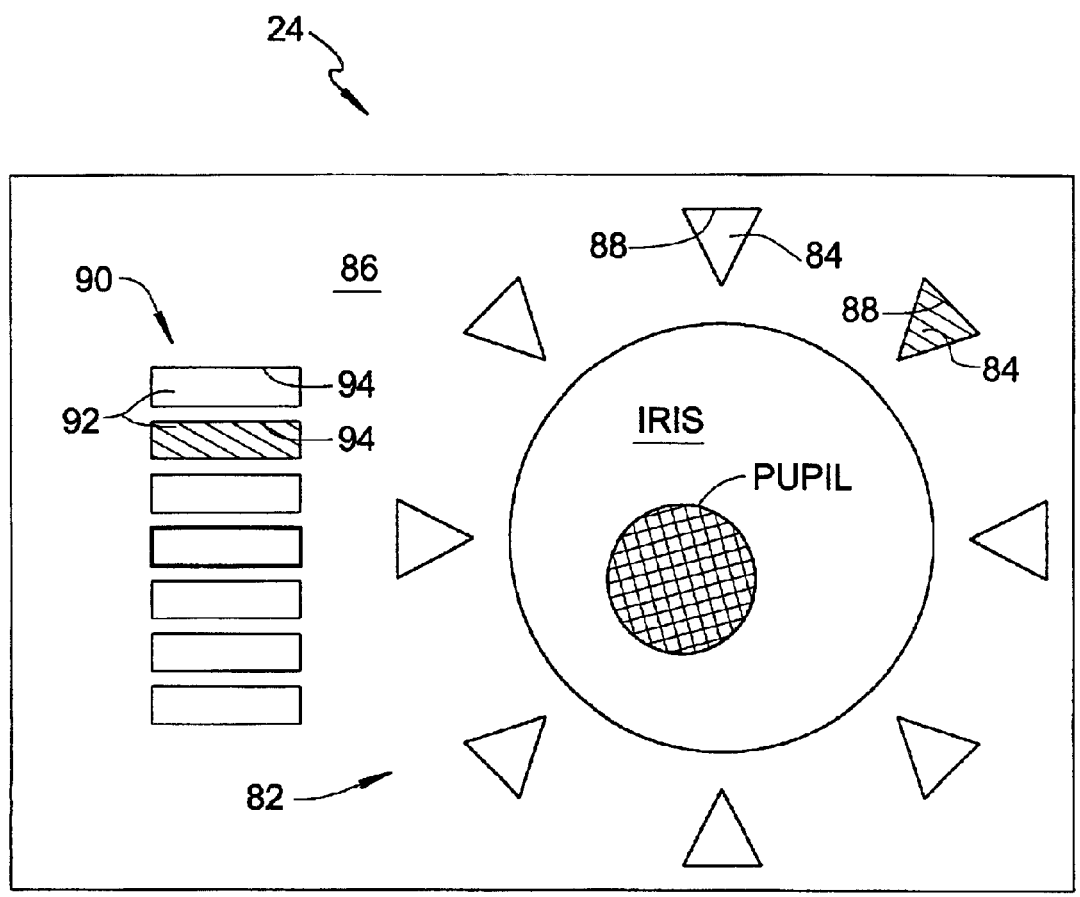
FIG. 8 is an enlarged view of a heads-up display forming part of the alignment system of the present invention for providing alignment instructions to an operator for aligning the instrument relative to an eye to be tested.

FIG. 8 shows an enlarged view of heads-up display 24 of instrument 10 and eye E as they appear to an operator viewing through eyepiece 22 along optical axis 14. Display 24 assists the operator in aligning the instrument by presenting the computed X-Y-Z alignment status in a format that instructs the operator regarding movement of the instrument necessary to achieve alignment. Heads-up display 24 comprises a polar array 82 of light-emitting diodes 84 masked by an overlay 86 having light-transmitting directional pointers 88 for providing an X-Y alignment instruction to the operator. The LEDs 84 in polar array 82 are each connected to microprocessor 60 by way of an I²C line 61 and a serial-to-parallel converter (not shown), whereby the LEDs are selectively illuminated depending upon the X-Y alignment status of the instrument relative to the eye. In particular, an LED 84 is illuminated corresponding to an appropriate directional pointer instructing the operator of the direction to move the instrument to align optical axis 14 with corneal vertex V. When X-Y alignment is achieved, all the LEDs 84 in polar array 82 can be illuminated in continuous or pulsing fashion to communicate a condition of X-Y alignment to the operator. Heads-up display 24 further comprises a linear array 90 of light-emitting diodes 92 positioned to correspond with light-transmitting rectangles 94 in overlay 86 for purposes of Z-axis alignment. The LEDs 92 in linear array 90 are each connected to microprocessor 60 by way of I²C line 61 and a serial-to-parallel converter (not shown), whereby the LEDs are selectively illuminated depending upon the Z alignment status of the instrument relative to the eye. More specifically, and by way of non-limiting example, the top and bottom LEDs in linear array 90 are the same color (i.e. red), the middle LED is another color (i.e. green), and the LEDs between the top Led and middle LED and between the bottom LED and the middle LED are all yet another color (i.e. yellow). When the instrument is too close to the eye, both red LEDs flash as a warning to the operator. The lower red and yellow LEDs indicate the instrument should be moved away from the eye, while the upper red and yellow LEDs indicate the instrument should be moved toward the eye. The green LED indicates that Z-axis alignment is reached. Currently, it is preferred to provide LEDs 84 and 92 on a single circuit board, and to use photographic film to form overlay 86, which may be separated from the LED circuit board by a spacer (not shown).

In the embodiment shown in FIG. 1, the actual heads-up display 24 is located in the instrument at a location off of optical axis 14. An image of heads-up display 24 is presented to the operator along optical axis 14 by means of mirror 26, beamsplitter 28, and an eyelens 17 within eyepiece 22. The X-Y polar array 82 is arranged circumferentially about a macro image of the patient's eye, whereby the operator can see the pupil and surrounding iris along with superimposed instructional display cues provided by heads-up display 24. For example, in FIG. 8, the operator is being instructed to move the instrument lower and to the left for X-Y alignment, and closer to the eye for Z alignment. In the embodiment shown, heads-up display 24 and mirror 26 are positioned such the display is confocal with eye E when ophthalmic instrument 10 is at a working distance, for example firing distance D, from the eye along optical axis 14. Eyelens 17 is chosen to image both the display and the eye at infinity for viewing by a relaxed eye. For example, in an instrument where proper X, Y, and Z alignment of the instrument relative to eye E places the eye at 250 mm from eyelens 17, the eyelens is preferably chosen to have a power of +4 diopters. As will be appreciated by those skilled in the art, when instrument 10 is positioned such that the observed eye E is in the range of Z-axis positions for which the position detection system is optimized (i.e. firing distance D+/−2.00 mm), the operator will see a clearly focused image of both display 24 and eye E at unit magnification.

Figure 9:
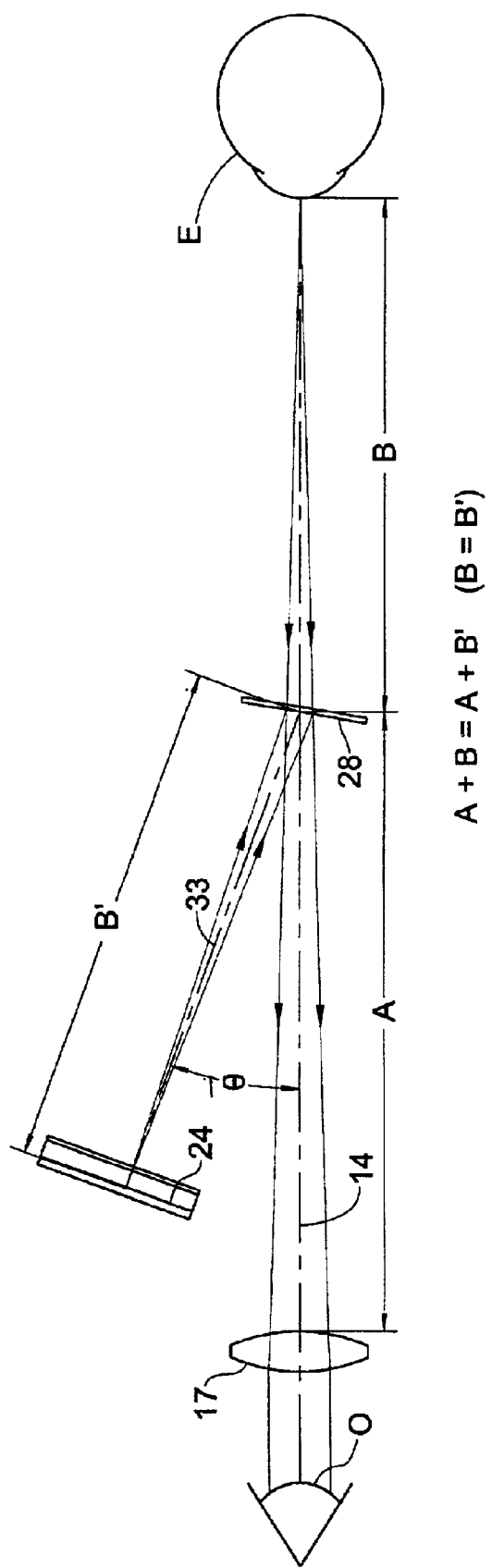
FIG. 9 is an optical schematic diagram of a heads-up display system formed in accordance with a currently preferred embodiment of the present invention.

FIG. 9 is an optical schematic diagram of a currently preferred heads-up display system pursuant to the present invention. In the system of FIG. 9, display 24 faces in a direction of a display axis 33 that forms an angle θ with optical axis 14 that is less than 90°. Most preferably, the angle θ is less than 30° and as close to 0° as possible without having the display 24 interfere with vision along optical axis 14. In a commercial embodiment, θ is equal to 20°. Accordingly, beamsplitter 28 is orientated such that it faces in a direction bisecting the angle θ formed by display axis 33 and optical axis 14, whereby light coming from display 24 along display axis 33 will be reflected by beamsplitter 28 and travel toward operator along optical axis 14. By way of non-limiting example, beamsplitter 28 may be in the form of a partially reflective mirror. The confocal relationship of display 24 and eye E is maintained as indicated in FIG. 9, where distance A+B to the eye is equal to distance A+B' to the display.

Figure 10:
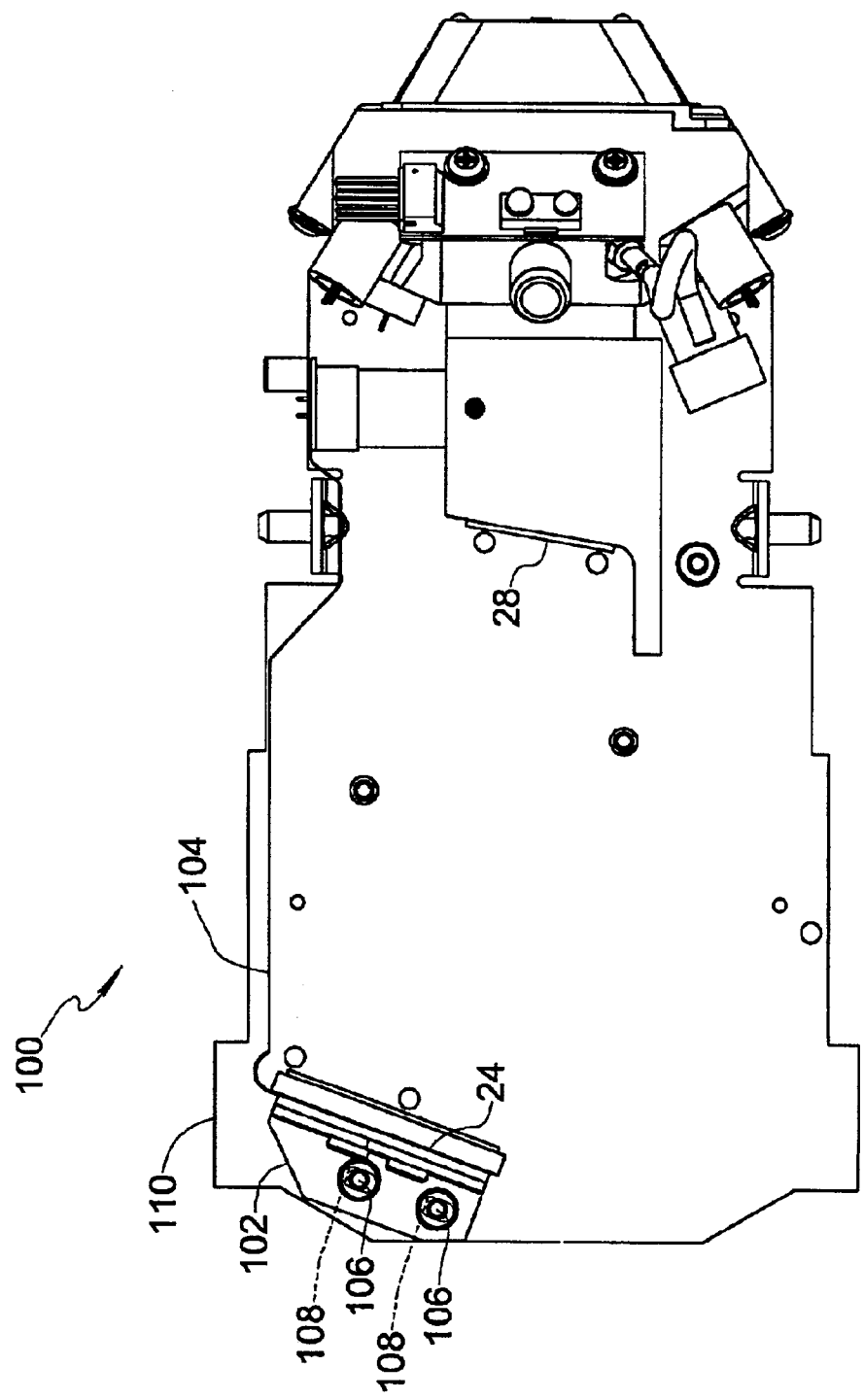
FIG. 10 is a plan view of an optical block portion of an ophthalmic instrument incorporating the heads-up display system shown schematically in FIG. 9.

FIG. 10 shows an optical block assembly 100 on which heads-up display 24 and beamsplitter 28 are mounted during assembly of instrument 10. Heads-up display 24 is fixed to a vertical portion of an angle bracket 102, and a horizontal portion of the angle bracket is fastened to a sheet metal platform 104 by a pair of screws 106 extending through respective slots 108 in platform 104. Slots 108 are elongated in a direction parallel to the plane of heads-up display 24 to permit the display to be properly aligned relative to beamsplitter 28, as this is critical to centering a reflected image of polar array 82 on optical axis 14. Platform 104 is fastened to an optical block 110 of assembly 100.

As will be appreciated, the heads-up display system shown in FIGS. 9 and 10 has certain advantages over the system shown in FIGS. 1 and 2. The angle at which display axis 33 intersects optical axis 14 is kept at a practical minimum, thereby saving space and reducing the problem of second surface reflections from beamsplitter 28 so that special coatings or an expensive pellicle beamsplitter are not needed. Also, mirror 26 is eliminated from the system.

Figure 11:
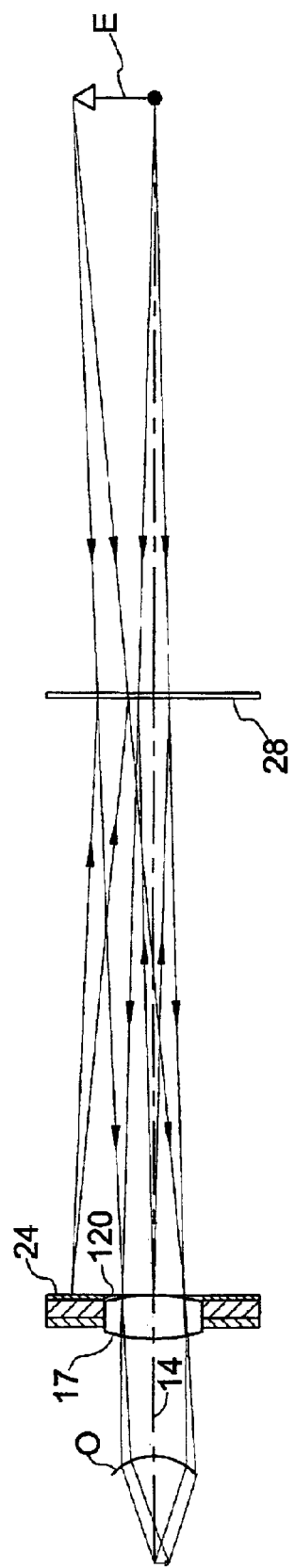
FIG. 11 is an optical schematic diagram of a heads-up display system formed in accordance with an alternative embodiment of the present invention wherein an instructive display is located about an eyelens of the system.

FIG. 11 schematically illustrates a possible alternative heads-up display system for assisting an operator during alignment of ophthalmic instrument 10. In the system of FIG. 11, heads-up display 24 includes a circular hole 120 corresponding to an interior area of polar array 82, and display 24 is positioned on optical axis 14 with eyelens 17 being received by hole 120 such that display 24 surrounds eyelens 17. Beamsplitter 28 can be a partially reflective mirror arranged orthogonally with respect to optical axis 14 such that eye E is viewed in transmission and display 24 is viewed in reflection.

Figure 12:
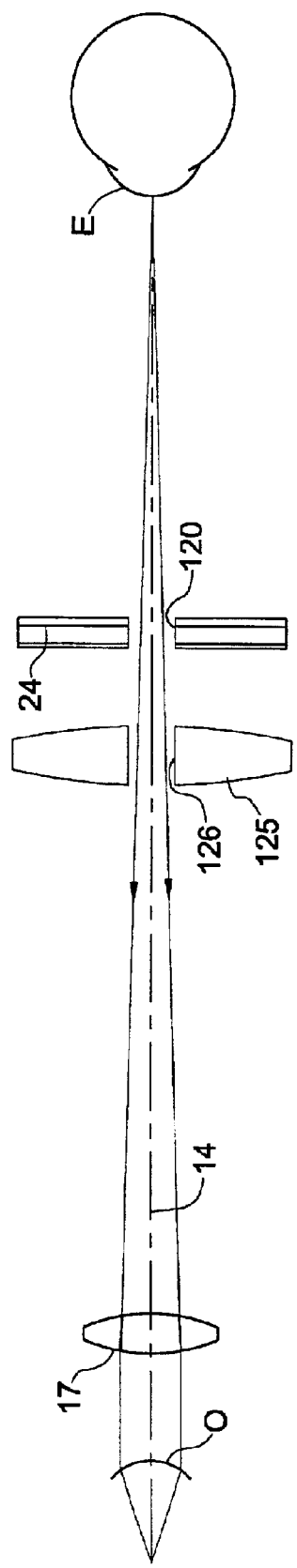
FIG. 12 is an optical schematic diagram of a heads-up display system formed in accordance with another alternative embodiment of the present invention wherein an instructive display is located between an eyelens of the system and the patient's eye.

Another possible configuration of a heads-up display system is shown schematically in FIG. 12. The system of FIG. 12 is a bifocal system wherein display 24 is mounted on optical axis and includes a light transmissive area in the form of hole 120 and corresponding to an interior area of polar array 82, such that viewing along optical axis 14 is not obstructed. An annular lens 125 having a central aperture 126 focuses the display image while allowing light from eye E to pass along optical axis 14.

What is claimed is:

1. An ophthalmic instrument comprising:
    an optical axis;
    opto-electronic position detection means for providing signal information indicative of the alignment status of said instrument relative to said eye;
    a display giving visual alignment cues based on said signal information; and
    an eyelens on said optical axis for imaging said eye and said display at infinity for simultaneous viewing by an operator.

2. The ophthalmic instrument according to claim 1, wherein said instrument includes a measurement axis for alignment in X and Y directions relative to said eye.

3. The ophthalmic instrument according to claim 2, wherein said instrument includes a reference point along said measurement axis for alignment in a Z direction at a working distance from said eye.

4. The ophthalmic instrument according to claim 3, wherein said display is confocal with said eye when said ophthalmic instrument is aligned in said X, Y, and Z directions.

5. The ophthalmic instrument according to claim 4, wherein said display is located off said optical axis, and said instrument further comprises a beamsplitter on said optical axis for reflecting an image of said display along said optical axis.

6. The ophthalmic instrument according to claim 5, wherein said display faces in a direction of a display axis, and said display axis forms an angle with said optical axis that is less than 90°.

7. The ophthalmic instrument according to claim 5, wherein said instrument further comprises a mirror for reflecting an image of said display to said beamsplitter.

8. The ophthalmic instrument according to claim 7, wherein said display faces in a direction of a display axis, and said display axis is parallel to said optical axis.

9. The ophthalmic instrument according to claim 5, wherein said display is mounted in said instrument by slotted means for allowing adjustment of the position of said display relative to said beamsplitter.

10. The ophthalmic instrument according to claim 9, wherein said slotted means comprises a platform having a pair of slots, an angle bracket having a pair of threaded fastener holes, and a pair of threaded fasteners respectively extending through said pair of slots for mating within said threaded fastener holes, said platform being located at a fixed position relative to said beamsplitter.

11. The ophthalmic instrument according to claim 4, wherein said display surrounds said eyelens.

12. The ophthalmic instrument according to claim 3, wherein said instrument comprises an annular display lens on said optical axis having a central aperture therethrough, said display is located along said optical axis between said eye and said display lens and includes a light transmitting area, said optical axis passes through said central aperture of said display lens and said light transmitting area of said display, and said display lens focuses an image of said display.

13. The ophthalmic instrument according to claim 3, wherein said display includes a polar array giving cues for X-Y direction alignment of said measurement axis relative to said eye and a linear array giving cues for Z direction alignment of said reference point relative to said eye.

14. The ophthalmic instrument according to claim 13, wherein an image of said polar array is centered on said optical axis.

15. The ophthalmic instrument according to claim 2, wherein said display includes a polar array giving cues for X-Y direction alignment of said of said measurement axis relative to said eye.

16. The ophthalmic instrument according to claim 15, wherein an image of said polar array is centered on said optical axis.

17. The ophthalmic instrument according to claim 1, wherein said eye and said display are viewed at unit magnification by said operator.

18. A display system for guiding an operator of an ophthalmic instrument in aligning said instrument relative to an eye of a patient, said display system comprising:
    an optical axis;
    a display giving visual alignment cues based on signal information indicative of the alignment status of said instrument relative to said eye; and
    an eyelens on said optical axis for imaging said eye and said display at infinity for simultaneous viewing by an operator.

19. The display system according to claim 18, wherein said display is confocal with said eye when said ophthalmic instrument is aligned relative to said eye.

20. The display system according to claim 19, wherein said display is located off said optical axis, and said display system further comprises a beam splitter on said optical axis for reflecting an image of said display along said optical axis.

21. The display system according to claim 20, wherein said display faces in a direction of a display axis, and said display axis forms an angle with said optical axis that is less than 90°.

22. The display system according to claim 21, wherein said display axis forms an angle with said optical axis that is less than 30°.

23. The display system according to claim 19, wherein said display includes a polar array giving cues for X-Y direction alignment of said instrument relative to said eye.

24. The display system according to claim 23, wherein an image of said polar array is centered on said optical axis.

25. The display system according to claim 19, wherein said display includes a polar array giving cues for X-Y direction alignment of said instrument relative to said eye and a linear array giving cues for Z direction alignment of said instrument relative to said eye.

26. The display system according to claim 25, wherein an image of said polar array is centered on said optical axis.

27. The display system according to claim 18, wherein said eye and said display are viewed at unit magnification by said operator.

* * * * *